US008293838B2

(12) United States Patent
Zhang et al.

(10) Patent No.: US 8,293,838 B2
(45) Date of Patent: Oct. 23, 2012

(54) STABLE AND STERILE TISSUE ADHESIVE COMPOSITION WITH A CONTROLLED HIGH VISCOSITY

(75) Inventors: Sheng Zhang, Hudson, NC (US); Rafael Ruiz, Hudson, NC (US)

(73) Assignee: Adhezion Biomedical, LLC, Wyomissing, PA (US)

( * ) Notice: Subject to any disclaimer, the term of this patent is extended or adjusted under 35 U.S.C. 154(b) by 666 days.

(21) Appl. No.: 12/214,791

(22) Filed: Jun. 20, 2008

(65) Prior Publication Data

US 2009/0318583 A1 Dec. 24, 2009

(51) Int. Cl.

| | |
|---|---|
| ***A61K 31/231*** | (2006.01) |
| ***A61K 31/215*** | (2006.01) |
| ***A61K 31/22*** | (2006.01) |
| ***A61K 31/765*** | (2006.01) |
| ***C08K 5/315*** | (2006.01) |
| ***C08J 3/215*** | (2006.01) |

(52) U.S. Cl. .......... 524/612; 524/81; 524/500; 514/519; 514/526; 514/527; 523/111; 523/118; 522/136; 424/78.37

(58) Field of Classification Search .................. 524/612, 524/81, 500; 514/519, 526, 527; 523/111, 523/118; 522/136; 424/78.37
See application file for complete search history.

(56) References Cited

U.S. PATENT DOCUMENTS 211,104 A 1/1879 Mulford
334,046 A 1/1886 Pinkham
1,221,227 A 4/1917 Schulz
1,229,195 A 6/1917 Hamilton
1,234,844 A 7/1917 Williams
1,822,566 A 9/1931 Davies
2,333,070 A 10/1943 Hoey et al.
2,721,858 A 10/1955 Joyner et al.
2,794,788 A 6/1957 Coover, Jr. et al.
2,912,454 A 11/1959 McKeever
3,152,352 A 10/1964 Kosik, Jr.
3,254,111 A 5/1966 Hawkins et al.
3,260,637 A 7/1966 von Bramer
3,282,773 A 11/1966 Wicker, Jr. et al.
3,324,855 A 6/1967 Heimlich
3,393,962 A 7/1968 Andrews
3,451,538 A 6/1969 Trementozzi
3,523,628 A 8/1970 Colvin et al.
3,524,537 A 8/1970 Winter
3,527,224 A 9/1970 Rabinowitz
3,527,841 A 9/1970 Wicker, Jr. et al.
3,540,577 A 11/1970 Trementozzi et al.
3,564,078 A 2/1971 Wicker, Jr. et al.
3,579,628 A 5/1971 Gander et al.
3,607,542 A 9/1971 Leonard et al.
3,614,245 A 10/1971 Schwartzman
3,667,472 A 6/1972 Halpern
3,692,752 A 9/1972 Setsuda et al.
3,742,018 A * 6/1973 O'Sullivan .................... 558/307
3,779,706 A 12/1973 Nablo
3,797,706 A 3/1974 Mule
3,836,377 A * 9/1974 Delahunty .................... 526/205
3,863,014 A 1/1975 Mottus
3,903,055 A 9/1975 Buck
3,924,623 A 12/1975 Avery
3,941,488 A 3/1976 Maxwell
3,975,422 A 8/1976 Buck
3,995,641 A 12/1976 Kronenthal et al.
4,003,942 A 1/1977 Buck
4,012,402 A 3/1977 Buck
4,013,703 A 3/1977 Buck
4,038,345 A 7/1977 O'Sullivan et al.
4,041,063 A 8/1977 Buck
4,042,442 A 8/1977 Dombroski et al.
4,057,535 A 11/1977 Lipatova et al.
4,102,945 A 7/1978 Gleave
4,105,715 A 8/1978 Gleave
4,109,037 A 8/1978 Nohara
4,142,630 A 3/1979 Hayes et al.
4,170,585 A * 10/1979 Motegi et al. ................. 524/762
4,171,416 A 10/1979 Motegi et al.
4,182,823 A 1/1980 Schoenberg
4,265,948 A 5/1981 Hayes et al.
4,310,509 A 1/1982 Berglund et al.
4,323,557 A 4/1982 Rosso et al.
4,328,170 A 5/1982 Okawara et al.

(Continued)

FOREIGN PATENT DOCUMENTS

DE 2 261 261 7/1973

(Continued)

OTHER PUBLICATIONS

Fussnegger, B. Lutrol F 68 (Poloxamer 188); BASF, Nov. 1999.*
MSDS of isobutyl-2-cyanoacrylate; Sep. 25, 1998.*
MSDS of n-butyl-2-cyanoacrylate; Oct. 19, 2009.*
MSDS of 2-octyl cyanoacrylate; Jun. 2, 2004.*
"Aclar® /Barex® Laminates: Flexible Solutions for Pharma Packaging" Drug Delivery Technology vol. 3, No. 3, May 2003, Posted on Mar. 28, 2008, http://www.drugdeliverytech.com/ME2/dirmod.asp?sid=&nm=&type=Publishing&mod=Publications%3A%.
Borrel et al. "The Effect of Crown Ethers, Tetraalkylammonioum Salts, and Polyoxyethylene Amphiphiles on Pirarubicin Incorporation in K562 Resistant Cells" Biochemical Pharmacology, vol. 50, No. 12., pp. 2069-2076, 1995.

(Continued)

*Primary Examiner* — Michael Pepitone
(74) *Attorney, Agent, or Firm* — Stradley Ronon Stevens & Young, LLP

(57) ABSTRACT

A stable and sterile adhesive composition with a controlled level of high viscosity is disclosed in the present invention. Adhesive compositions with different ranges of viscosity could be prepared by heating the adhesive monomer composition at mild temperature in the presence of pluronic polymer. The viscosity of the adhesive composition is able to be controlled to any desired level. A method of stabilizing the adhesive composition with a desired level of high viscosity is provided by using the combination of free radical and acid stabilizers. Methods for packaging, sterilizing and applying the adhesive in the medical field are also provided.

50 Claims, No Drawings

U.S. PATENT DOCUMENTS

| | | | |
|---|---|---|---|
| 4,340,043 | A | 7/1982 | Seymour |
| 4,364,876 | A | 12/1982 | Kimura et al. |
| 4,374,126 | A | 2/1983 | Cardarelli et al. |
| 4,377,490 | A | 3/1983 | Shiraishi et al. |
| 4,386,193 | A | 5/1983 | Reich et al. |
| 4,413,753 | A | 11/1983 | Stock |
| 4,439,196 | A | 3/1984 | Higuchi |
| 4,444,933 | A | 4/1984 | Columbus et al. |
| 4,447,224 | A | 5/1984 | DeCant, Jr. et al. |
| 4,447,233 | A | 5/1984 | Mayfield |
| 4,460,759 | A | 7/1984 | Robins |
| 4,475,916 | A | 10/1984 | Himmelstein |
| 4,480,940 | A | 11/1984 | Woodruff |
| 4,486,194 | A | 12/1984 | Ferrara |
| 4,487,603 | A | 12/1984 | Harris |
| 4,533,422 | A | 8/1985 | Litke |
| 4,542,012 | A | 9/1985 | Dell |
| 4,551,366 | A | 11/1985 | Maruhashi et al. |
| 4,554,686 | A | 11/1985 | Baker |
| 4,643,181 | A | 2/1987 | Brown |
| 4,646,765 | A | 3/1987 | Cooper et al. |
| 4,649,909 | A | 3/1987 | Thompson |
| 4,652,763 | A | 3/1987 | Nablo |
| 4,685,591 | A | 8/1987 | Schaefer et al. |
| 4,713,235 | A | 12/1987 | Krall |
| 4,718,966 | A | 1/1988 | Harris et al. |
| 4,772,148 | A | 9/1988 | Buschemeyer |
| 4,786,534 | A | 11/1988 | Aiken |
| 4,818,325 | A | 4/1989 | Hiraiwa et al. |
| 4,925,678 | A | 5/1990 | Ranney |
| 4,959,217 | A | 9/1990 | Sanders et al. |
| 4,977,892 | A | 12/1990 | Ewall |
| 4,978,527 | A | 12/1990 | Brink et al. |
| 4,994,542 | A | 2/1991 | Matsuda et al. |
| 5,009,654 | A | 4/1991 | Minshall et al. |
| 5,039,753 | A | 8/1991 | Woods et al. |
| 5,042,690 | A | 8/1991 | O'Meara |
| 5,051,256 | A | 9/1991 | Barnes |
| 5,069,907 | A | 12/1991 | Mixon et al. |
| 5,083,685 | A | 1/1992 | Amemiya et al. |
| 5,131,777 | A | 7/1992 | Kimura et al. |
| 5,135,964 | A | 8/1992 | Lee et al. |
| 5,167,616 | A | 12/1992 | Haak et al. |
| 5,169,383 | A | 12/1992 | Gyory et al. |
| 5,192,536 | A | 3/1993 | Huprich |
| 5,225,182 | A | 7/1993 | Sharma |
| 5,232,774 | A | 8/1993 | Otsuka et al. |
| 5,236,703 | A | 8/1993 | Usala |
| 5,240,525 | A | 8/1993 | Percec et al. |
| 5,254,132 | A | 10/1993 | Barley et al. |
| 5,283,034 | A | 2/1994 | Okrongly et al. |
| 5,288,159 | A | 2/1994 | Wirt |
| 5,302,629 | A | 4/1994 | Berejka |
| 5,306,490 | A | 4/1994 | Barley, Jr. |
| 5,312,864 | A | 5/1994 | Wenz et al. |
| 5,328,687 | A | 7/1994 | Leung et al. |
| 5,344,670 | A | 9/1994 | Palmer et al. |
| 5,350,798 | A | 9/1994 | Linden et al. |
| 5,358,349 | A | 10/1994 | Burroughs et al. |
| 5,370,221 | A | 12/1994 | Magnusson et al. |
| 5,403,591 | A | 4/1995 | Tighe et al. |
| 5,411,345 | A | 5/1995 | Ueji et al. |
| 5,453,457 | A | 9/1995 | Meltzer et al. |
| 5,457,141 | A | 10/1995 | Matsuda et al. |
| 5,470,597 | A | 11/1995 | Mendenhall |
| 5,475,110 | A | 12/1995 | Hudkins et al. |
| 5,480,935 | A | 1/1996 | Greff et al. |
| 5,530,037 | A | 6/1996 | McDonnell et al. |
| 5,547,662 | A | 8/1996 | Khan et al. |
| 5,561,198 | A | 10/1996 | Huver et al. |
| 5,665,817 | A | 9/1997 | Greff et al. |
| 5,684,042 | A | 11/1997 | Greff et al. |
| 5,730,994 | A | 3/1998 | Askill et al. |
| 5,749,956 | A | 5/1998 | Fisher et al. |
| 5,803,086 | A | 9/1998 | Scholz et al. |
| 5,807,563 | A | 9/1998 | Askill et al. |
| 5,874,044 | A | 2/1999 | Kotzev |
| 5,902,594 | A | 5/1999 | Greff et al. |
| 5,916,882 | A | 6/1999 | Jeng |
| 5,928,611 | A | 7/1999 | Leung |
| 5,944,754 | A | 8/1999 | Vacanti |
| 5,957,877 | A | 9/1999 | Askill et al. |
| 5,979,450 | A | 11/1999 | Baker et al. |
| 5,981,621 | A | 11/1999 | Clark et al. |
| 5,985,395 | A | 11/1999 | Comstock et al. |
| 5,998,472 | A | 12/1999 | Berger et al. |
| 6,086,906 | A | 7/2000 | Greff et al. |
| 6,090,397 | A | 7/2000 | Lee et al. |
| 6,099,807 | A | 8/2000 | Leung |
| 6,136,326 | A | 10/2000 | Kotzev |
| 6,143,352 | A | 11/2000 | Clark et al. |
| 6,143,805 | A | 11/2000 | Hickey et al. |
| 6,155,265 | A | 12/2000 | Hammerslag |
| 6,217,603 | B1 | 4/2001 | Clark et al. |
| 6,228,354 | B1 | 5/2001 | Jeng |
| 6,245,933 | B1 | 6/2001 | Malofsky et al. |
| 6,248,800 | B1 | 6/2001 | Greff et al. |
| 6,294,629 | B1 | 9/2001 | O'Dwyer et al. |
| 6,299,631 | B1 | 10/2001 | Shalaby |
| 6,310,166 | B1 | 10/2001 | Hickey et al. |
| 6,323,275 | B2 | 11/2001 | Takahashi et al. |
| 6,352,704 | B1 * | 3/2002 | Nicholson et al. ............ 424/407 |
| 6,488,665 | B1 | 12/2002 | Severin et al. |
| 6,492,434 | B1 | 12/2002 | Barley, Jr. et al. |
| 6,495,229 | B1 | 12/2002 | Carte et al. |
| 6,547,917 | B1 | 4/2003 | Misiak et al. |
| 6,579,469 | B1 | 6/2003 | Nicholson et al. |
| 6,620,846 | B1 | 9/2003 | Jonn et al. |
| 6,626,296 | B1 | 9/2003 | Jimu et al. |
| 6,667,031 | B2 | 12/2003 | Azevedo |
| 6,699,940 | B2 | 3/2004 | Shalaby |
| 6,742,522 | B1 | 6/2004 | Baker et al. |
| 6,743,858 | B2 | 6/2004 | Hickey et al. |
| 6,746,667 | B2 | 6/2004 | Badejo et al. |
| 6,767,552 | B2 | 7/2004 | Narang |
| 6,779,657 | B2 | 8/2004 | Mainwaring et al. |
| 6,797,107 | B1 | 9/2004 | Kotzey |
| 6,802,416 | B1 | 10/2004 | D'Alessio et al. |
| 6,849,082 | B2 | 2/2005 | Azevedo |
| 6,881,421 | B1 * | 4/2005 | da Silveira et al. ........... 424/489 |
| 6,896,838 | B2 | 5/2005 | D'Alessio |
| 6,942,875 | B2 | 9/2005 | Hedgpeth |
| 6,960,040 | B2 | 11/2005 | D'Alessio et al. |
| 6,974,585 | B2 | 12/2005 | Askill |
| 6,977,278 | B1 | 12/2005 | Misiak |
| 6,995,227 | B2 | 2/2006 | Ryan et al. |
| 7,255,874 | B1 | 8/2007 | Bobo et al. |
| 2002/0002223 | A1 | 1/2002 | Cox et al. |
| 2002/0037272 | A1 * | 3/2002 | Askill et al. ............... 424/78.35 |
| 2003/0044380 | A1 | 3/2003 | Zhu et al. |
| 2003/0077386 | A1 | 4/2003 | Azevedo |
| 2003/0135016 | A1 | 7/2003 | Tajima et al. |
| 2003/0158579 | A1 | 8/2003 | Azevedo |
| 2003/0158580 | A1 | 8/2003 | Azevedo |
| 2004/0115274 | A1 | 6/2004 | Cox et al. |
| 2004/0126355 | A1 | 7/2004 | Childers |
| 2004/0127738 | A1 | 7/2004 | Azevedo |
| 2004/0253039 | A1 | 12/2004 | Stenton |
| 2005/0047846 | A1 | 3/2005 | Narang et al. |
| 2005/0067312 | A1 | 3/2005 | Gupta et al. |
| 2005/0142163 | A1 | 6/2005 | Hunter et al. |
| 2005/0147582 | A1 | 7/2005 | Zimmerman et al. |
| 2005/0182347 | A1 | 8/2005 | Bishop et al. |
| 2005/0196431 | A1 | 9/2005 | Narang et al. |
| 2005/0197421 | A1 | 9/2005 | Loomis |
| 2005/0281866 | A1 | 12/2005 | Jarrett et al. |
| 2005/0284487 | A1 | 12/2005 | Gellerstedt et al. |
| 2006/0062687 | A1 | 3/2006 | Morales |
| 2007/0041935 | A1 | 2/2007 | Salamone et al. |
| 2007/0048356 | A1 | 3/2007 | Schorr et al. |
| 2007/0078207 | A1 * | 4/2007 | Jonn et al. .................... 524/347 |
| 2007/0092481 | A1 | 4/2007 | Misiak et al. |
| 2007/0092483 | A1 | 4/2007 | Pollock |
| 2007/0147947 | A1 | 6/2007 | Stenton et al. |
| 2008/0021139 | A1 | 1/2008 | Blacklock et al. |
| 2008/0078413 | A1 | 4/2008 | Padget et al. |
| 2008/0102053 | A1 | 5/2008 | Childers |

2008/0319063 A1 12/2008 Zhang
2009/0317353 A1 * 12/2009 Zhang et al. ............... 424/78.06
2010/0035997 A1 2/2010 Broadley et al.
2010/0269749 A1 10/2010 Badejo et al.

FOREIGN PATENT DOCUMENTS

| | | |
|---|---|---|
| DE | 40 09 621 | 10/1991 |
| DE | 2010 3336 | 5/2001 |
| DE | 10 2007 019 044 | 10/2008 |
| EP | 0127466 | 12/1984 |
| EP | 0271675 | 6/1988 |
| FR | 2700698 | 7/1994 |
| GB | 1230560 | 5/1971 |
| GB | 2200124 | 7/1988 |
| JP | 59-066471 | 4/1984 |
| JP | 62-022877 | 1/1987 |
| JP | 03-207778 | 9/1991 |
| JP | 10-140091 | 5/1998 |
| WO | WO96/14292 | 5/1996 |
| WO | WO96/23532 | 8/1996 |
| WO | WO99/10020 | 3/1999 |
| WO | WO03/070257 | 8/2003 |
| WO | WO2004/045498 | 6/2004 |
| WO | WO2006/073922 | 7/2006 |
| WO | WO2009/003017 | 12/2008 |
| WO | WO2009/064291 | 5/2009 |

OTHER PUBLICATIONS

Cameron, J.L. et al., "The degradation of cyanoacrylate tissue adhesive, pt. 1", Surgery, vol. 58, Iss. 2, Aug. 1965, pp. 424-430.

Collins et al., "Biological Substrates and Cure Rates of Cyanoacrylate Tissue Adhesives" Archives of Surgery vol. 93, Sep. 1966, 428-432.

Darwish et al., "The evaluation of crown ether based niosomes as cation containing and cation sensitive drug delivery systems" International Journal of Pharmaceutics 159 (1997) 207-213.

Dumont et al., "New Oligosaccharidic Crown Ethers as Potential Drug-Targetting Vectors: Synthesis & Biological Evaluation" Bioorganic & Medicinal Chemistry Letters, vol. 4, No. 9, pp. 1123-1126, 1994.

Garnier-Suillerot et al., "Analysis of Drug Transport Kinetics in Multidrug-resistant Cells: Implications for Drug Action" Current Medicinal Chemistry, 2001, 8 51-64.

Hansen et al. "Fast Cure—High moisture vapor transmission rate adhesives improve wound care." Adhesives Age Mar. 22-25, 2003, Lehman, R.A.W. et al., "Toxicity of Alkyl 2-Cyanoacrylates", Archives of Surgery, vol. 93, Issue 3, Sep. 1966, pp. 441-446.

Leonard, F, "Hemostatic Applications of Alpha Cyanoacrylates: Bonding Mechanism and Physiological Degradation of Bonds", Adhesion in Biological Systems, ed. R.S. Manly, 1970, pp. 185-199.

Leonard, F. et al., "Interfacial Polymerization of n-Alkyl a-Cyanoacrylate Homologs", Journal of Applied Polymer Science, vol. 10 1966, pp. 1617-1623.

Leonard, F. et al., "Synthesis and Degradation of Poly (alkyl a-Cyanoacrylates)", Journal of Applied Polymer Science, vol. 10, Iss 8, Aug. 1966, p. 1214.

Leonard, F. et al., "Synthesis and Degradation of Poly(alkyl a-Cyanoacrylates)", Journal of Applied Polymer Science, vol. 10, 1966, pp. 259-272.

Tseng, Y.C. et al., "Modification of synthesis and investigation of properties for 2-cyanoacrylates", Biomaterials, vol. 11, Jan. 1990, pp. 73-79.

Uchegbu et al., "Non-ionic surfactant based vesicles (niosomes) in drug delivery" International Journal of Pharmaceutics 172 (1998) 33-70.

Vezin, W.R. et al., "Diffusion of Small Molecules in Poly-n-Alkyl Cyanoacrylates", British Pharmaceutical Conference 1978—Communications presented at the 115th meeting, Coventry, Sep. 11-15, 1978, Journal of Pharmacy and Pharmacology, vol. 30, Issue: Suppl, Dec. 1978, p. 2P.

Vezin, W.R. et al., "In vitro heterogeneous degradation of poly(n-alkyl a-cyanoacrylates)", Journal of Biomedical Materials Research, vol. 14, 1980, pp. 93-106.

Woodward, S.C. et al., "Histotoxicity of Cyanoacrylate Tissue Adhesives in the Rat", Annals of Surgery, vol. 162, No. 1, Jul. 1965, pp. 113-122.

Yonezawa, M. et al., "Studies on a-Cyanoacrulate, VI: Reaction of Cyanoacetate with Formaldehyde" Yuki Gosei Kagaku Kyokaishi, vol. 25 (4) Apr. 1967, pp. 311-316.

* cited by examiner

STABLE AND STERILE TISSUE ADHESIVE COMPOSITION WITH A CONTROLLED HIGH VISCOSITY

BACKGROUND OF THE INVENTION

1. Field of the Invention

The present invention relates to stabilized, sterilized cyanoacrylate adhesive compositions with the controlled level of high viscosity, methods of making these compositions and to their use for medical applications.

2. Description of Related Art

Cyanoacrylate esters are well known to be adhesives and have been used extensively in different fields due to their quick bonding and applicability to a large range of substrates. They are used as industrial and structural adhesives, consumer product for repair of household items and in the hobby sector for assembly and repair. In addition, cyanoacrylate compositions have found application in medicine for closing wounds especially in cases where suturing does not provide satisfactory results. Cyanoacrylate esters are used in protecting surface injuries including abrasions, lacerations, sores, burns and other open surface wounds. In spite of their interesting properties and wide applications in different fields, cyanoacrylate monomers have disadvantages which prevent use of cyanoacrylates in certain fields. For example, the inherent low viscosity of cyanoacrylate monomers in medical applications may result in the spreading of the adhesive into undesired areas as a consequence of the cyanoacrylate adhesive's runniness. In addition, the runniness of the cyanoacrylate monomer makes it difficult to prevent the adhesive from entering the wound, which will adversely affect the healing of the wound.

In order to obtain a cyanoacrylate adhesive composition with a desired level of higher viscosity, different thickening agents and methods have been employed. Thickening agents, such as polymers have been used to improve the viscosity of the cyanoacrylate adhesive compositions. The polymer additives are soluble in cyanoacrylate compositions either at room or elevated temperature.

Misiak et al., U.S. Pat. Appl. No. 20070092481, disclose a thickened cyanoacrylate adhesive composition by using poly [butyleneterephthalate-co-poly(ethyleneglycol) terephthalate] as a viscosity modifier. The formulation of cyanoacrylate adhesives as low viscosity emulsions, non-flowable and gels forms can be prepared by adding this polymer component to cyanoacrylate compositions. The viscosity of the composition is dependent upon the nature and level of the polymer material used in the composition. Kotzey et al. U.S. Pat. No. 6,797,107 disclose a solid cyanoacrylate adhesive composition which can be applied to a substrate in solid form and which polymerizes into an adhesive polymer upon liquefying. The solid cyanoacrylate composition liquefies at temperatures slightly above room temperature and polymerizes upon liquification. $\epsilon$-caprolactones are used as a solidifying polymer with cyanoacrylate monomers and other additives to form the solid cyanoacrylate adhesive composition.

Hickey et al. U.S. Pat. No. 6,743,858 disclose a method of making a thickened sterile monomeric adhesive composition Preparation of the composition includes placing a mixture of a polymerizable monomer and a thickening agent in a container, sealing the container and sterilizing the container and the mixture. The thickening agent is soluble in the monomer at room temperature. Suitable thickeners employed include, for example, polyoxalates, lactic-glycolic acid copolymers, polycaprolactone, lactic acid-caprolactone copolymers, poly (caporolactone+DL-lactide+glycolide), polyorthoesters, polyalkyl acrylates, copolymers of alkylacrylate and vinyl acetate, polyalkyl methacrylates, and copolymers of alkyl methacrylates and butadiene.

Shalaby U.S. Pat. No. 6,299,631 discloses a bioabsorbable adhesive/hemostatic formulation of a 2-alkoxyalkylcyanoacrylate with trimethylene carbonate-based polymers as the viscosity thickener.

Greff et al. disclose, in U.S. Pat. No. 5,665,817, alkyl cyanoacrylate compositions suitable for topical application to human skin, which comprise a suitable amount of the thickening agent to increase the viscosity. The thickening agent used is biocompatible materials that increase the viscosity of the alkyl cyanoacrylate composition, which include polymethylmethacrylate (PMMA) or other preformed polymers soluble in the alkyl cyanoacrylate. The thickening agent is added to provide a viscosity of from about 2 to 50,000 centipoises (cp) at 20° C.

Linden et al. U.S. Pat. No. 5,350,789 disclose 2-cyanoacrylate-based tissue adhesives employing biocompatible oxalate polymers as reactive plasticizers and thickening agents. The adhesives are capable of being formulated to allow modulus matching of the adhesive and the substrate.

Leung et al. U.S. Pat. No. 5,328,687 disclose adhesive compositions which contain thickening agents that may be used for bonding tissue. Polymer thickeners employed include polylactic acid, polyglycolic acid, lactic-glycolic acid copolymers, polycaprolactone, lactic acid-caprolactone copolymers, poly-3-hydroxybutyric acid, polyorthoesters, polyalkyl acrylates, copolymers of alkylacrylate and vinyl acetate, polyalkyl methacrylates, and copolymers of alkyl methacrylates and butadiene.

O'Sullivan et al. U.S. Pat. No. 4,038,345 disclose stable cyanoacrylate adhesive compositions having improved viscosities. The adhesive compositions have viscosities in excess of about 500 centipoises comprising at least one monomeric ester of 2-cyanoacrylic acid, and a polyacrylate thickener which is pretreated to have a reduced viscosity greater than about 5 cp. A free radical polymerization initiator is used in the amount of less than about one percent by weight. The composition also contains an inhibitor of the anionic polymerization of the monomer. O'Sullivan discloses a process for preparing improved cyanoacrylates which involves heating a conventional polyacrylate thickener at a suitable temperature and for a suitable period of time to reduce its content of free radical polymerization initiators to below about one percent; and dissolving a sufficient amount of polymer thickener in the adhesive monomer to produce a cyanoacrylate adhesive composition with suitable viscosity.

Gleave discloses in U.S. Pat. No. 4,102,945, a cyanoacrylate adhesive composition thickened by a copolymer or terpolymer resin capable of being dissolved or solvated by the cyanoacrylate monomer exhibits significantly improved peel strength. Polymer thickeners are acrylonitrile-butadiene-styrene terpolymers, methacrylate-butadiene-styrene terpolymers, and vinylidene chloride-acrylonitrile copolymers.

Setsuda et al. U.S. Pat. No. 3,692,752 disclose thickened cyanoacrylate solutions containing certain polyether acrylates/methacrylates, acrylic/methacrylic esters of bis(hydroxyalkyl) phosphonic acid derivatives, and acrylic/methacrylic esters of tris(hydroxyalkyl) cyanuric acid derivatives.

Wicker et al. disclose, in U.S. Pat. No. 3,527,841, 2-cyanoacrylate adhesive compositions for general and particular for surgical uses containing poly (lactic acid) as a viscosity thickener and an acidic compound such as sulfur dioxide and a free radical stabilizer such as hydroquinone.

Wicker U.S. Pat. No. 3,282,773, discloses cyanoacrylate adhesive compositions in which poly (methylmethacrylate) was used as the thickener.

Polymer of cyanoacrylates has also been used to increase the viscosity of the cyanoacrylate adhesive compositions. U.S. Pat. Appl. No. 20060062687 to Morales discloses a method of sterilizing 2-cyanoacrylate compositions with poly-cyanoacrylate as the thickener, including heating the composition in a device at a temperature of from about 70 to about 140° C. for an effective amount of time. Morales discloses sterilized 2-cyanoacrylate ester compositions for use in medicine or surgery. Morales also discloses a method for assaying the sterilization of cyanoacrylate compositions.

U.S. Pat. No. 3,564,078 discloses the use of poly (ethyl 2-cyanoacrylate) as a component of cyanoacrylate compositions. U.S. Pat. No. 3,527,224 to Rabinowitz discloses a surgical adhesive composition comprising monomeric and polymeric n-pentyl cyanoacrylate obtained by free-radical polymerization. U.S. Pat. No 2,794,788 teaches thickening of cyanoacrylate adhesives by dissolving polymeric alkyl cyanoacrylates, as well as other compounds including methacrylates, polyacrylates and cellulose esters.

Organic or inorganic powders, which are not soluble in cyanoacrylate monomer, have also been used as fillers to adjust the viscosity of cyanoacrylate compositions. Such materials include various inert inorganic materials such as silica, quartz, alumina, calcium and metal salts and organic powders such as polycarbonates, polyvinylidene fluorides, polyethylenes, and other polymeric powders. For example, U.S. Pat. No. 4,533,422 discloses cyanoacrylate compositions which employ fumed silicas as the filler are stable and exhibit a high thixotropic ratio. U.S. Pat. No. 3,607,542 discloses the preparation of a water-resistant cyanoacrylate paste containing insoluble, inert fillers such as salts of calcium, titanium, zinc, tin, aluminum, iron and copper, among others. U.S. Pat. No. 4,105,715, discloses the use of finely divided organic powders such as polycarbonates, polyvinylidene fluorides, polyethylenes, and other polymeric powders are proposed as additives for cyanoacrylates. Blending insolvable materials with cyanoacrylate compositions can cause separation while the adhesive is stored, resulting in ineffective modification of the viscosity. Also, the presence of the fillers can sometimes affect the quality of the bonding.

The use of polymer additives to improve the viscosity of cyanoacrylate adhesives presents different disadvantages. Relatively small modification of the viscosity was achieved by using polymer additive as the viscosity modifer. The amount of the polymer thickener is limited due to the poor solubility of certain polymers in the cyanoacrylate monomer so that it was difficult to obtain highly viscous adhesives. Increasing the amount of polymer thickener incorporated would result in spinnability, reduction of optical clarity and weakening of the adhesive bond. In addition, many polymer additives used as the thickener undergo decomposition under sterilization conditions, which lead to the decrease of the viscosity. Such instability becomes more obvious when the cyanoacrylate adhesive compositions are stabilized by acids, due to the fact that those acids destabilize the polymer thickener in the compositions. Curing or further polymerization of the cyanoacrylate adhesive occurs during the process of sterilization even in the presence of certain amounts of stabilizers. Sometimes polymerization induced by the sterilization is so serious that the cyanoacrylate compositions are no longer usable. In other cases, the shelf life of the sterilized cyanoacrylate compositions can be dramatically shorten even though these sterilized adhesive compositions are still usable. Presently, the only acceptable polymer thickener which can be successfully used for commercial cyanoacrylate adhesive compositions include poly(methylmethacrylate) or poly(vinylacetate). Therefore it would be desirable to provide a simple and effective method to prepare cyanoacrylate compositions with the controllable viscosity without sacrificing the shelf life stability of the cyanoacrylate compositions.

SUMMARY OF THE INVENTION

The present invention provides a stable and sterile cyanoacrylate adhesive composition with a controllable level of high viscosity, a method of preparing cyanoacrylate adhesive compositions with different range of viscosity, a method of packaging and sterilizing the cyanoacrylate adhesive, as well as a procedure of stabilizing the cyanoacrylate adhesive with the desired level of high viscosity using a combination of stabilizers.

The present invention provides a method of controlling the viscosity level of cyanoacrylate adhesive composition. Cyanoacrylate adhesive compositions with different levels of viscosity are prepared by heating the cyanoacrylate monomer composition at mildly elevated temperature in the presence of a small amount of pluronic polymer. The desired level of viscosity can be controlled by modifying the amount of polymer additive and the free radical or anionic stabilizers in the cyanoacrylate monomer. On the other hand, highly viscous cyanoacrylate gel prepared according to the present invention can be further diluted with cyanoacrylate monomers to provide cyanoacrylate adhesive compositions with the desired level of viscosity, which represents another way to control the viscosity level of the cyanoacrylate adhesive composition.

The present invention provides a method of stabilizing cyanoacrylate adhesive compositions with different levels of viscosity by applying at least one free radical stabilizer and at least one acid stabilizer to the adhesive. In more preferred embodiments of the present invention, at least two free radical stabilizers and at least two acid stabilizers are used to stabilize the adhesive composition. The cyanoacrylate compositions with the combination of stabilizers disclosed in preferred embodiments of this invention provide at least two year shelf life after the sterilization.

The present invention provides a method of packaging the cyanoacrylate adhesive composition with the controlled level of high viscosity, which is stabilized with the combination of free radical and anion polymerization inhibitors. The cyanoacrylate adhesive compositions can be packaged in different applicators, which are then sterilized. Cyanoacrylate adhesive composition with the controlled level of viscosity can be uniformly dispensed onto the substrates from the applicator.

The present invention provides a method of preparing the sterile cyanoacrylate adhesive composition with the desired level of viscosity by sterilizing the composition after introducing the pluronic polymer additive. The sterile and stable cyanoacrylate adhesive composition with a biocompatible polymer additive is especially suitable to be used in the medical field.

The present invention provides a method of sealing tissue by spreading the sterilized cyanoacrylate adhesive composition with a desired level of high viscosity onto the tissue from the applicator, which is quickly cured to seal the tissue. Other advantages of the current invention will become obvious as disclosed in the detailed descriptions.

DETAILED DESCRIPTION OF PREFERRED EMBODIMENTS

According to the invention, a stabilized and sterilized cyanoacrylate adhesive composition with the desired level of high viscosity is provided. Cyanoacrylate compositions with different levels of viscosity are obtained by heating cyanoacrylate monomer in the presence of pluronic polymer to partially polymerize the cyanoacrylate monomer. The level of the viscosity of cyanoacrylate compositions is readily controlled by modifying the amount of pluronic polymer and polymerization inhibitor present in the cyanoacrylate monomer. The cyanoacrylate adhesive composition with the desired level of viscosity is then stabilized with the combination of one or more free radical and acid stabilizers. The further polymerization of the cyanoacrylate compositions with the desired level of high viscosity can be inhibited by using the combination of free radical and acid stabilizers in spite of the presence of pluronic polymer as the polymerization initiator. The cyanoacrylate compositions thus stabilized are stable for at least two years shelf life after packaging in the applicator and sterilization. The cyanoacrylate adhesive compositions with a desired level of high viscosity can be packaged with different applicators, which are then sterilized using different sterilization methods. Such stable and sterile cyanoacrylate adhesive compositions with the desired level of high viscosity can be used as medical tissue adhesive for sealing and aiding in the repair of tissue.

According to the present invention, cyanoacrylate adhesive compositions with the desired level of high viscosity can be prepared by heating the cyanoacrylate monomer in the presence of pluronic polymer. The cyanoacrylate monomer becomes partially polymerized by the pluronic polymer's addition and then the partial polymerization is quenched by adding stabilizers to the compositions to provide the desired level of viscosity. Cyanoacrylate adhesive compositions with the desired level of viscosity can also be prepared by diluting highly viscous cyanoacrylate compositions (eg. thick gel materials prepared according to the present invention) with cyanoacrylate monomers.

Pluronics, the tradename for poloxamers, are nonionic triblock copolymers composed of a central hydrophobic chain of polyoxypropylene flanked by two hydrophilic chains of polyoxyethylene. Because the lengths of the polymer blocks can be customized, many different poloxamers exhibit slightly different properties. For the generic term poloxamer these copolymers are commonly named with the letter "P" followed by three digits, the first two digits times 100 gives the approximate molecular mass of the polyoxypropylene core and the last digit times 10 gives the percentage polyethylene content (e.g. P407=poloxamer with a polyoxypropylene molecular mass of 4000 g/mole and a 70% polyoxyethylene content). For the Pluronic tradename, coding of these copolymers starts with a letter to define its physical form (L=liquid, P=paste, F=flake (solid)) followed by two or three digits. The first digit(s) refer to the molecular mass of the polyoxypropylene core (determined from BASF's Pluronic grid) and the last digit times 10 gives the percentage polyoxyethylene content (e.g. Pluronic F127=pluronic with a polyoxypropylene molecular mass of 4000 g/mol and a 70% polyoxyethylene content. Therefore P407 defines the same poloxamer as Pluroninc F127. The general structure of pluronic polymer is shown in below.

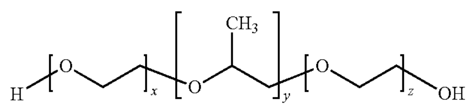

Structure of pluronic polymer a-Hydro-w-hydroxypoly(oxyethylene)$_x$poly(oxypropylene)$_y$poly(oxyethylene)$_z$block polymer The chart below demonstrates some of the possible values of x, y and z for poloxamers.

| Poloxamer | x | y | z |
|---|---|---|---|
| 124 | 12 | 20 | 12 |
| 188 | 80 | 27 | 80 |
| 237 | 64 | 37 | 64 |
| 338 | 141 | 44 | 141 |
| 407 | 101 | 56 | 101 |

The pluronic polymers utilized in this invention include preferably pluronic F38 prill, pluronic F68 prill, pluronic F88, pluronic F108NF and pluronic F127 prill, in the preferable amount 0.02 to 0.5%. Any other suitable pluronic polymer additive, such as, but not limited to, pluronic 10R5, pluronic 17R2, pluronic 17R4, pluronic 25R2, pluronic 25R4, pluronic 31R1, pluronic F68 LF, pluronic F68NF, pluronic F68 NF prill poloxamer 188, pluronic F77, pluronic F87, pluronic F98, pluronic F108, pluronic F127, pluronic F127 NF, pluronic F127 NF prill poloxamer407, pluronic L 10, pluronic L 101, pluronic, L121, pluronic L 31, pluronic L 35, pluronic, L 43, pluronic L44, pluronic, L44 NF poloxamer 124, pluronic, L 61, pluronic 62, pluronic L62 LF, pluronic, L 62D, pluronic L64, pluronic L 81, pluronic L 92, pluronic N 3, pluronic P 103, pluronic P 104, pluronic P 105, pluronic P 123 surfactant, pluronic P 65, pluronic, P 84 and pluronic P 85, can also be used. (Pluronic polymers were obtained from BASF Corporation, 100 Campus Drive, Florham Park, N.J., USA) The use of biocompatible pluronic polymers as additives makes the cyanoacrylate adhesive compositions of the current invention especially suitable for medical use. Pluronic polymers such as pluronic F127 are preferred additives for medical applications as this pluronic polymer has been approved by FDA for medical use and they are biocompatible.

The amount of pluronic polymer added to the cyanoacrylate monomer depends upon the required level of viscosity and the presence of stabilizers in the cyanoacrylate monomer. The pluronic polymer additive is preferably present in an amount of about 0.01% to about 0.50% by weight of cyanoacrylate compositions. In preferred embodiments, the pluronic polymer additive is present in an amount of about 0.04% to about 0.30%, and more preferably in an amount of about 0.07% to about 0.16%.

The present invention provides a method of preparing cyanoacrylate ester compositions with the desired level of viscosity using a combination of polymer additive and cyanoacrylate mixed at an elevated temperature. Pluronic polymer is not soluble in 2-cyanoacrylate adhesive compositions at room temperature. However, it may be dissolved at mildly elevated temperatures in the range of about 30 to about 70° C., preferably from about 40 to about 65° C., and more preferably from about 50 to about 60° C. Dissolution of pluronic polymer in cyanoacrylate monomer induces the partial polymerization of the cyanoacrylate monomer to increase the viscosity of the composition to a desired level.

The mixing temperature also affects the performance of the cyanoacrylate compositions. In order to evaluate the effect of temperature, cyanoacrylate adhesive compositions were prepared at different temperatures in the presence of the pluronic polymer. In most of the cases, the partial polymerization induced by the pluronic polymer occurs at about 40 to about 60° C. to provide cyanoacrylate adhesives with a desired level of viscosity.

Pluronic polymers are mild polymerization initiators and partial polymerization can be controlled by modifying the amount of pluronic polymer and polymerization inhibitor in the cyanoacrylate monomer. Preferably, cyanoacrylate monomer pre-stabilized with a certain amount of free radical and acid stabilizer is partially polymerized to provide the adhesive composition with the desired level of viscosity.

The present invention provides a process for making cyanoacrylate adhesive compositions with the desired level of high viscosity while reducing undesired side reactions and inhibiting the further polymerization of the compositions by using a combination of free radical and acid stabilizers to provide an extended shelf life after sterilization. It is well known that cyanoacrylate monomer is extremely sensitive to premature polymerization. Once polymerization is initiated, curing of the adhesive can be very rapid, which makes it very difficult to control the polymerization rate after the initiation of the polymerization. This creates the challenge of thickening cyanoacrylate adhesive compositions via partially polymerizing the cyanoacrylate monomer. The present invention provides a method to overcome such challenge by heating the cyanoacrylate monomer at the temperature range of 30-70° C., preferably 40-65° C., and more preferably 50-60° C. in the presence of pluronic polymer for a time period from about 1.0 to about 2.5 hours. The pluronic polymers used in the present invention are difunctional block copolymer surfactant terminating in primary hydroxyl groups. The very small percentage of hydroxyl group in the molecule may make the pluronic polymer a mild polymerization initiator for cyanoacrylate monomer The polymerization rate can be readily controlled by modifying the amount of pluronic polymer and polymerization inhibitor present in the cyanocrylate monomer.

The present invention provides methods of controlling the viscosity level of the cyanoacrylate adhesive compositions. Cyanoacrylate adhesive compositions with the desired level of viscosity can be prepared by modifying the amount of polymer additive and the free radical or anion polymerization inhibitor. According to the present invention, cyanoacrylate compositions with various viscosities, including compositions which are gels and non-flowable forms can be obtained. Extremely viscous cyanoacrylate gel obtained according to the present invention can be further diluted with cyanoacrylate monomers to prepare cyanoacrylate adhesive compositions with the desired level of viscosity. Cyanoacrylate gel is the jelly-like and highly viscous liquid cyanoacrylate with reduced mobility compared to cyanoacrylate monomer. Cyanoacrylate gels prepared according to the present invention have a viscosity in the range of about 1000 to about 300,000 cp, preferably from about 1000 to about 100,000 cp, more preferably from aobut 1000 to about 50,000 cp and even more preferably from about 1000 to about 30,000 cp.

According to the present invention, the viscosity level of the cyanoacrylate adhesive compositions can be controlled. The viscosity level of the cyanoacrylate adhesive compositions is determined by many factors such as the amount of pluronic polymer, the amount of stabilizer present in the cyanoacrylate monomer, the mixing temperature and the mixing time before quenching the partial polymerization of the cyanoacrylate. The viscosity level of the cyanoacrylate adhesive compositions is dependent upon the rate of partial polymerization of cyanoacrylate. Therefore, to increase the viscosity of the cyanoacryalte adhesive one can increase the amount of pluronic polymer, decrease the amounts of the stabilizers, increase the mixing temperature and increase the mixing time Introducing a predetermined amount of pluronic polymer is into the cyanoacrylate monomer (without or with stabilizers) and mixing the pluronic polymer with the cyanoacrylate monomer to homogeneity at mildly elevated temperatures initiates the partial polymerization of cyanoacrylate. The viscosity of the cyanoacrylate adhesive composition increases as the polymerizaiton of the cyanoacrylate monomer proceeds. Compared to the cyanoacrylate monomer in the absence of stabilizers, the partial polymerization rate of the cyanoacrylate monomer pre-stabilized with stabilizer is easier to control, as is the viscosity level of cyanoacrylate adhesive composition. Once the partial polymerization of cyanoacrylate monomer is initiated, polymerization will continue until it is quenched by the addition of stabilizers. In the preferred embodiments of the present invention, the viscosity of the cyanoacrylate adhesive composition may be determined using a viscometer and once a desired level of viscosity is reached stabilizers may be immediately added to quench the polymerization so that the viscosity of said cyanoacrylate compositions can be stabilized at the desired level. The quenching of the partial polymerization may be accomplished by the addition of free radical stabilizer, anionic stabilizer and/or the combination of free radical and anionic stabilizer. In embodiments of the present invention, the free radical stabilizer is, but not limited to butylated hydroxyl anisole (BHA). BHA may be used in an amount of about 200 to about 15000 ppm of cyanoacrylate compositions preferably about 1000 to about 10000 ppm, more preferably about 2000 to about 8000 ppm. The preferred anionic stabilizer is, but not limited to sulfur dioxide in an amount of about 2 to about 500 ppm, preferably about 10 to about 200 ppm.

Cyanoacrylate adhesive compositions prepared according to the preferred embodiments of the present invention for use in medical applications have a viscosity such that the adhesive stops running, flowing beyond the intended application site or is substantially prevented from dripping into the wound. The adhesive may adversely affect the healing of the wound if the adhesive runs into the wound. This is due to the fact that adhesive inside the wound may act as a barrier to two edges of the wound thereby preventing closure of the wound. On the other hand, cyanoacrylate adhesive compositions should not be so viscous as to block its application to the skin, such as when the adhesive is applied through an applicator. Adhesive compositions with viscosity of less than 3,000 centipoise (cp) are normally employed for medical applications such as wound closure. More preferably the adhesive compositions for medical applications such as wound closure having a viscosity of less than 2,000 cp are employed. In a more preferred embodiment, the viscosity of the adhesive compositions is in the range of from about 10 to about 1000 cp, preferably from about 20 to about 500 cp and more preferably from about 30 to about 300 cp, including from about 30 cp to about 200 cp, from about 40 cp to about 200 cp, from about 50 cp to about 200 cp, from about 60 cp to about 200 cp, from about 70 cp to about 200 cp, from about 80 cp to about 200 cp, from about 90 cp to about 200 cp, from about 100 cp to about 200 cp, from about 150 cp to about 200 cp, from about 200 cp to about 300 cp and from about 250 cp to about 300 cp.

The present invention also provides stable cyanoacrylate adhesive compositions with a desired level of viscosity. The stability of the cyanoacrylate adhesive compositions may be evaluated by the accelerated aging and viscosity test. The accelerated aging test of cyanoacrylate adhesive composition is performed in the oven at 80° C. for a period of 12 days. The cyanoacrylate compositions are tested for viscosity at intervals of 3, 6, 9 and 12 days. Based on prior stability studies for cyanoacrylate compositions and ASTM method, 12 days accelerated aging at 80° C. correlates to 2 years of shelf life at ambient temperatures (ASTM F1980-2). The accelerated aging test at 80° C. is initially conducted for bulk cyanoacrylate adhesive compositions with the desired level of high viscosity before packaging and sterilizating. Table 1 shows the viscosity result of the cyanoacrylate compositions at day 0 and day 12 of the accelerated aging test at 80° C. The viscosity of the cyanoacrylate adhesive compositions increases after the accelerated aging but viscosities of the aged samples at day 12 are in the acceptable range of 10 to 3000 cp, preferably 20 to 3000 cp and more preferably 30 to 2000 cp. In the more preferred embodiments the viscosity of the adhesive composition after the accelerated aging test is only slightly changed from the initial viscosity testing at day 0. The viscosity of the adhesive composition even after aging will be acceptable as long as the adhesive is still dispensable via an applicator and the adhesives perform as intended. The use of the cyanoacrylate adhesive will dictate the absolute range of increased or decreased viscosity acceptable during aging, but in preferred embodiments the viscosity of the composition at day 12 of aging at 80° C. is within about 100% (no change in viscosity) to 500% (five times the viscosity) of the viscosity of the composition at day 0 (before accelerate aging testing). In preferred embodiments the viscosity of the composition at day 12 of aging at 80° C. is within about 100% to 250% of the viscosity of the composition at day 0 (before accelerate aging testing) and in more preferred embodiments the viscosity of the composition at day 12 of aging at 80° C. is within about 100% to 150% of the viscosity of the composition at day 0 (before accelerate aging testing) In fact, the increase of the viscosity of the cyanoacrylate adhesive compositions after the accelerated aging test is not drastic, indicating that the bulk adhesive compositions before packaging and sterilizing are stable.

TABLE 1

Viscosity of cyanoacrylate adhesive compositions at day 0 and day 12 of the accelerated aging at 80° C.

| | | Average viscosity (cp) of the compositions before and after the accelerated aging at 80° C. | |
|---|---|---|---|
| Entry | Composition[a] | Day 0 | Day 12 |
| 1a | OCA + 0.04% F127 | 50.5 | 73.5 |
| 1b | OCA + 0.2% F68 | 116.3 | 206.2 |
| 1c | OCA + 0.16% F68 | 40.7 | 67.4 |
| 1d | OCA + 0.15% F68 | 39.2 | 71.5 |
| 1e | OCA + 0.145% F68 | 32.5 | 54.4 |
| 1f | 33.8% OCA gel in OCA monomer | 84.5 | 90.7 |

[a]Octyl cyanoacrylate (OCA) monomer is pre-stabilized with different amount of stabilizers.

The present invention provides sterile and stable cyanoacrylate adhesive compositions with the desired level of high viscosity. In addition to being stable, cyanoacrylate adhesive compositions should be sterile for medical use. According to the present invention, cyanoacrylate adhesive compositions with the desired level of viscosity may be sterilized. This is also an advantage of the present invention, as most of the prior cyanoacrylate compositions with polymer additives were not sterilized. The sterilization can be accomplished by common techniques, and is preferably accomplished by methods including, but not limited to, chemical, physical, and irradiation methods. Examples of chemical methods include, but are not limited to, exposure to ethylene oxide. Examples of irradiation methods include, but are not limited to, gamma irradiation, electron beam irradiation, and microwave irradiation. Preferred methods of sterilizing the cyanoacrylate compositions of the present invention are chemical sterilization and electron beam sterilization.

As confirmed by the accelerated aging test at 80° C. for 12 days, the bulk cyanoacrylate adhesive compositions with the desired level of viscosity are relatively stable prior to sterilization. However, the performance of cyanoacrylate adhesive compositions can be drastically affected by the sterilization. Curing or further polymerization of the cyanoacrylate adhesive occurs during the process of sterilization even in the presence of stabilizers. Sometimes polymerization induced by the sterilization is so serious that the cyanoacrylate compositions are no longer usable. In other cases, the shelf life of the sterilized cyanoacrylate compositions can be dramatically shorten even though these sterilized adhesive compositions are still usable.

In order to solve the instability problem induced by the sterilization, the present invention provides a method of stabilizing cyanoacrylate adhesive compositions with the desired level of high viscosity by adding a combination of at least one free radical stabilizer and at least one acid stabilizer to the cyanoacrylate compositions. In more preferred embodiments of the present invention, at least two free radical stabilizers and at least two acid stabilizers are used to stabilize the adhesive composition. The combination of two or more free radical stabilizers and two or more acid stabilizers provides better stabilizing effects than the conventional combination of only one free radical and acid stabilizer. Compared to cyanoacrylate adhesive compositions with only one free radical stabilizer and/or one acid stabilizer, cyanoacrylate adhesive compositions with the desired level of high viscosity stabilized by the combination of at least two free radical stabilizers and at least two acid stabilizers inhibited effectively the sterilization-induced polymerization so that an extended shelf life can be obtained.

In embodiments of the present invention, the preferred primary free radical stabilizer is butylated hydroxyl anisole (BHA). BHA is used in an amount of about 200 to about 15000 ppm of cyanoacrylate compositions preferably about 1000 to about 10000 ppm, more preferably about 2000 to about 8000 ppm. In preferred embodiments, BHA is used in combination with at least one more free radical stabilizer including without limitation, hydroquinone; catechol; hydroquinone monomethyl ether and hindered phenols such as butylated hydroxyanisol; 4-ethoxyphenol; butylated hydroxytoluene (BHT, 2,6-di-tert-butyl butylphenol), 4-methoxyphenol (MP); 3-methoxyphenol; 2-tert-butyl-4methoxyphenol; 2,2methylene-bis-(4-methyl-6-tert-butylphenol). In preferred embodiments, hydroquinone, 4-methoxyphenol and butylated hydroxytoluene are used as second or additional free radical stabilizers. MP is used in an amount of about 1 to about 4000 ppm, preferably about 100 to about 2000 ppm. Hydroquinone is used in an amount of about 1 to about 2500 ppm, preferably from about 50 to about 1500 ppm. BHT is used in an amount of about 1 to about 10000 ppm, preferably from about 500 to about 5000 ppm. The amount to be used can be determined by one of ordinary skills in the art using known techniques without undue experimentation.

In certain embodiments of the present invention, the preferred primary acid stabilizer is sulfur dioxide in an amount of about 2 to about 500 ppm, preferably about 10 to about 200 ppm. The second or additional acid stabilizers may be a very strong acid including without limitation perchloric acid, hydrochloric acid, hydrobromic acid, toluenesulfonic acid, fluorosulfonic acid, phosphoric acid, ortho, meta, or para-phosphoric acid, trichloroacetic acid, and sulfuric acid. The very strong acid is used in an amount of about 1 to about 250 ppm, preferably from about 5 to about 50 ppm. Preferably, the very strong acid stabilizer is sulfuric acid, phosphoric acid or perchloric acid. More preferably, sulfuric acid is used as the additional strong acid stabilizer.

In other embodiments of the present invention, the second or additional acid stabilizers may be sultones or weak organic acids including, but not limited to, benzoic acid, cyanoacetic acid, chloroacetic acid and acetic acid. More preferably, 1,4-butane sultone or acetic acid is used as the additional acid stabilizer in an amount of from about 1 to about 1000 ppm, preferably from about 100 to about 500 ppm. Cyanoacrylate adhesive compositions with the desired level of high viscosity may be subjected to sterilization after the stabilization with the combination of different free radical and acid stabilizers. The performance of the adhesive compositions after the sterilization is dependent on how these compositions are prepared. According to the present invention, cyanoacrylate adhesive compositions with the desired level of high viscosity may be prepared such that even after sterilization the composition retains the desired viscosity. In the methods of the present invention where the cyanoacrylate compositions are prepared by heating the cyanoacrylate monomer in the presence of pluronic polymer, the viscosity of said compositions increases or remains the same, after the sterilization. The increase in viscosity can be controlled within a very small percentage by applying the suitable combination of free radical and acid stabilizers in the preferred embodiments. Therefore, the viscosity of the cyanoacrylate adhesive compositions can be readily targeted to a desired level even after sterilization.

In the methods of the present invention where the cyanoacrylate adhesive compositions with a desired level of high viscosity are prepared by diluting extremely viscous cyanoacrylate gel with cyanoacrylate monomer, the viscosity of the adhesive composition decreases, or remains the same, after the sterilization. The decrease in viscosity of the cyanoacrylate adhesive compositions is due to the degradation of the partial polymer of cyanoacrylate caused by the sterilization. The decrease in viscosity of the cyanoacrylate adhesive compositions, after the sterilization, varies depending on the original viscosity and the percentage of the cyanoacrylate gel in the compositions. The decrease in viscosity after sterilization can be drastic in certain circumstances. However, with the compositions of the present invention the change in viscosity can be controlled to an acceptable range. The use of the cyanoacrylate adhesive will dictate the absolute range of increased or decreased viscosity acceptable after sterilization but in preferred embodiments the viscosity of the composition after sterilization is within about 25% (one-quarter the viscosity) to 100% of the viscosity of the composition before sterilization. In preferred embodiments the viscosity of the composition after sterilization is within about 30% to 100% of the viscosity of the composition before sterilization and in more preferred embodiments the viscosity of the composition after sterilization is within about 50% to 100% of the viscosity of the composition before sterilization. As shown in Table 2, modifying the percentage of the cyanoacrylate gel and applying the suitable combination of free radical and acid stabilizers can control the change in viscosity that occurs upon sterilization.

TABLE 2

Viscosity of the cyanoacrylate adhesive compositions with the desired level of high viscosity before and after the sterilization.

| Entry[a] | Composition | Average viscosity (cp) Before sterilization | After sterilization |
|---|---|---|---|
| 2a | OCA + 0.14% F68 | 75.6 | 76.4 |
| 2b | OCA + 0.118% F68 | 56.4 | 60.7 |
| 2c | OCA + 0.112% F68 | 50 | 54.9 |
| 2d | 33.8% of OCA Gel in OCA | 77 | 44.1 |
| 2e | 49.5% of OCA Gel in OCA | 121.6 | 88.7 |
| 2f | 33.8% of OCA Gel in OCA | 69.5 | 40.7 |
| 2g | 28.5% of OCA Gel in OCA | 52.7 | 40.5 |
| 2h | 28.5% of OCA Gel in OCA | 54.4 | 39.2 |
| 2i | 49.5% of OCA Gel in OCA | 117.1 | 85.4 |

[a]High viscosity cyanoacrylate compositions from 2a to 2c were prepared directly by heating cyanoacrylate monomer in the presence of pluronic polymer. High viscosity cyanoacrylate compositions from 2d to 2i were prepared by diluting extremely viscous cyanoacrylate gel with cyanoacrylate monomer.

The present invention provides sterile and stable cyanoacrylate adhesive compositions with the desired level of high viscosity, which are compatible with suitable packaging. The said cyanoacrylate adhesive compositions may be packaged in high density polyethylene (HDPE) bottles and different applicators, and then sterilized. The stability of the sterilized cyanoacrylate adhesive compositions with the desired level of high viscosity in different packages is evaluated by the accelerated aging test. The accelerated aging test of the sterilized cyanoacrylate adhesive composition is performed in the oven at 80° C. for a period of 12 days. Table 3 summarizes the selected viscosity results of the sterilized cyanoacrylate adhesive compositions in different packages at day 0 and day 12 of the accelerated aging test performed at 80° C. By comparing the performance and viscosity of said compositions at day 0 with that at day 12 of the accelerated aging at 80° C., the sterilized cyanoacrylate adhesive compositions with the desired level of viscosity in various packages exhibit dramatically different stability. In certain embodiments of the present invention, some sterilized cyanoacrylate adhesive compositions are cured at as early as day 3 of the accelerated aging at 80° C. The shortened shelf life of such sterilized cyanoacrylate adhesive compositions might be due to the decomposition of free radical and/or acid stabilizer induced by sterilization. In more preferred embodiments, however, the sterilized cyanoacrylate adhesive compositions with the desired level of viscosity exhibit excellent stability with only a slight increase in viscosity at day 12 of the accelerated aging at 80° C. compared to that at day 0. Therefore, cyanoacrylate adhesive compositions with the desired level of high viscosity developed in the preferred embodiments of the present invention can be packaged and sterilized to provide at least two years shelf life by selecting suitable package and desired combinations of free radical and acid stabilizers.

TABLE 3

Performance of the sterilized cyanoacrylate compositions with the desired level of viscosity.

| Entry | Composition[a] | Plasticizer | Ave. viscosity (cp) before and after aging at 80° C. Day 0 | Day 12 | Comment |
|---|---|---|---|---|---|
| 3a | OCA + 0.11% F68 | 5% ATBC | 42.7 | N/A | Cured at day 12 |
| 3b | OCA + 0.105% F68 | 1% ATBC | 33.7 | 74.8 | |
| 3c | 33.8% of OCA gel in OCA monomer | N/A | 41.9 | 219.2 | |
| 3d | 34.7% of OCA gel in OCA monomer | 5% ATBC | 38.2 | 52.3 | |
| 3e | OCA + 0.11% F68 | 5% TBC | 41.1 | N/A | Too viscous to dispense |
| 3f | 28.5% of OCA gel in OCA monomer | N/A | 43.3 | 84 | |
| 3g | OCA + 0.1446% F68, | N/A | 95.2 | N/A | Cured at day 3 |
| 3h | OCA + 0.15% F127 | N/A | 140.2 | N/A | Cured at day 9 |
| 3i | 49.5% of OCA gel in OCA monomer | 5% ATBC | 85.2 | N/A | Too viscous to dispense |

[a]Final compositions with the desired viscosity are stabilized with at least two free radical stabilizers and at least two acid stabilizers in the varying amount.

According to certain embodiments of the present invention, a plasticizer may be included in the sterilized and stabilized cyanoacrylate adhesive compositions with the desired level of high viscosity. The plasticizing agent preferably does not contain any moisture and should not affect adversely the stability of the cyanoacrylate compositions. Examples of suitable plasticizers include, but are not limited to, tributyl citrate (TBC), acetyl tributyl citrate (ATBC), dimethyl sebacate, diethylsebacate, triethyl phosphate, tri(2-ethyl-hexyl)phosphate, tri(p-cresyl) phosphate, diisodecyl adipate (DIDA), glyceryl triacetate, glyceryl tributyrate, dioctyl adipate (DICA), isopropyl myrisate, butyl sterate, lauric acid, trioctyl trimelliate, dioctyl glutatrate (DICG) and mixtures thereof. Tributyl citrate, diisodecyl adipate and acetyl tributyl citrate are preferred plasticizer in an amount of 0 to 30%, preferably 1% to 20%, and more preferably 2% to 10%.

The effect of the amount of plasticizer on the performance of the cyanoacrylate adhesive compositions with the desired level of high viscosity has been evaluated. Table 4 shows the effect of plasticizer ATBC on the performance of the cyanoacrylate adhesive compositions. Cyanoacrylate adhesive compositions in Table 4 were stabilized with the same amount of free radical and acid stabilizers. However, the amount of plasticizer (ATBC) was varied. The decrease in viscosity of the adhesive compositions with different amount of ATBC is almost the same. However, the long term stability of the adhesive compositions is different for the adhesive compositions with different amount of plasticizer as confirmed by the accelerated aging at 80° C. for 12 days. The viscosity of the composition with 10% of plasticizer increases from about 40 cp at day 0 to about 208 cp at day 12 of the accelerated aging at 80° C. However, the viscosity of the adhesive compositions with less plasticizer increases from about 40 cp at day 0 to a maximum of 92 cp at day 12 of the accelerated aging at 80° C. These observations confirm that the presence of greater concentration of plasticizer adversely affect the stability of the adhesive compositions, probably because the plasticizer decomposes due to sterilization.

TABLE 4

Effect of plasticizer on the stability of the cyanoacrylate compositions.

| composition | Plasticizer (ATBC) | Average viscosity (cp) Before sterilization | After sterilization Day 0 | Day 12 at 80° C. |
|---|---|---|---|---|
| 4a | 0 | 52.7 | 43.3 | 84 |
| 4b | 1% | 54.4 | 39.2 | 91.8 |
| 4c | 5% | 53.1 | 40.0 | 88.3 |
| 4d | 10% | 52.1 | 39.4 | 208.2 |

Crown ether, an accelerator may be included in the sterile and stable cyanoacrylate adhesive compositions with the desired level of high viscosity. Examples of crown ether include, but are not limited to, 15-crown-5, 18-crown-6, dibenzo-18-crown-6, tribenzo-18-crown-6, dicyclohexyl-18-crown-6, benzo-15-crown-5, dibenzo-24-crown-8, dibenzo-30-crown-10, asym-dibenzo-22-crown-6, dimethylsila-11-crown-4, dimethylsila-14-crown-5, dimethylsila-17-crown-6, dibenzo-14-crown-4, dicyclohexyl-24-crown-8, asym-dibenzo-22-crown-6, cyclohexyl-12-crown-4, 1,2-decalyl-1 5-crown-5, 1,2-naphtho-15-crown-5, 3,4,5-naphthyl-16-crown-5, 1,2-methyl-benzo-18-crown-6, 1,2-methylbenzo-5, 6-methylbenzo-18-crown-6, 1,2-t-butyl-18-crown-6, 1,2-vinylbenzo-15-crown-5, 1,2-vinylbenzo-18-crown-6, 1,2-t-butyl-cyclohexyl-18-crown-6, and 1,2-benzo-1,4-benzo-5-oxygen-20-crown-7. The crown ether is used in an amount of 0 to 2000 ppm, preferably 50 to 1000 ppm, and more preferably 100 to 500 ppm. The amount to be used can be determined by one of ordinary skills in the art using known techniques without undue experimentation.

According to the present invention, the cyanoacrylate compositions may contain small amounts of dyes such as derivatives of anthracene and other complex structures. These dyes include without limitation, 1-hydroxy-4-[4-methylphenylamino]-9,10anthracenedione (D&C violet No. 2); 9-(o-carboxyphenyl)-6-hydroxy-2,4,5,7-tetraiodo-3H-xanthen-3-one-, disodium salt, monohydrate (FD&C Red No. 3); disodium salt of 6-hydroxy-5-[(4-sulfophenyl)axo]-2-naphthalene-sulfonic acid (FD&C Yellow No. 6,); and 2-(1,3dihydro-3-oxo-5-sulfo-2H-indole-2-ylidine)-2,3-dihydro-3-oxo-1H-ind-ole-5sulfonic acid disodium salt (FD&C Blue No. 2).

According to the present invention, the 2-cyanoacrylate monomer is preferably an aliphatic cyanoacrylate ester and more preferably an alkyl, cycloalkyl, alkenyl and alkoxyalkyl, 2-cyanoacrylate ester. The alkyl group may contain from 2 to 12 carbon atoms, and is preferably a $C_2$ to $C_8$ alkyl ester, and is more preferably a $C_4$ to $C_8$ alkyl ester. Suitable 2-cyanoacrylate esters include without limitation, the ethyl, n-propyl, iso-propyl, n-butyl, pentyl, hexyl, cyclohexyl, heptyl, n-octyl, 2-octyl, 2-ethylhexyl, 2-methoxyethyl and 2-ethoxyethyl esters. The cyanoacrylate monomer may be a single monomer type or may be mixtures of various monomer types.

In the embodiments of the present invention, cyanoacrylate gel can be prepared by using one cyanoacrylate monomer, which can be diluted with the mixture of other cyanoacrylate monomers for adhesive compositions with the desired level of high viscosity. The properties of the cyanoacrylate adhesive compositions can be modified by mixing different cyanoacrylate monomers. By introducing a cyanoacrylate monomer with a shorter alkyl chain to a cyanoacrylate monomer with a longer alkyl chain, the cure time and degradation rate of adhesive can be shortened and the tensile strength can be improved. Inversely, cyanoacrylate adhesive with a shorter alkyl chain will offer better flexibility by incorporating longer alkyl chain cyanoacrylate monomers. One preferred cyanoacrylate adhesive composition is prepared by diluting 2-octyl cyanoacrylate gel that is made according to the present invention with n-butyl cyanoacrylate monomer.

The 2-cyanoacrylate monomer used in the invention is synthesized based on the procedures known in the prior art by reacting cyanoacetate with formaldehyde in the presence of a basic condensation catalyst at elevated temperature to give a low molecular weight polymer. A depolymerization step followed under high temperature and high vacuum in the presence of acidic and anionic inhibitors, yielding a crude monomer that can be distilled under high temperature and high vacuum in the presence of radical and acidic inhibitors. The distilled 2-cyanoacrylate monomers are then formulated with free radical and acidic inhibitors depending upon their application to provide the necessary stability.

According to the present invention, cyanoacrylate adhesive compositions with the desired level of high viscosity may be packaged in, but not limited to, plastic applicator. The plastic applicator is composed of a reservoir container and a sponge application tip. The container part is preferably air and water tight with sealing that prevents contamination of the adhesive inside the applicator. The sponge tip is saturated with liquid adhesive once it is folded over so that adhesive can be dispensed uniformly onto the wound site. The container size and sponge tip can be varied dependent on the volume of the adhesive. Cyanoacrylate adhesive will polymerize very rapidly when it is stored in a very small amount. To prevent premature polymerization a minimum of about 0.1 mL to 4 mL, preferably 0.2 mL to 2 mL, and more preferably 0.3 mL to 1 mL of adhesive should be packaged in the applicator. In order to extend the shelf life, the volume of the container is preferably about 50 to 80 percent and more preferably 60 to 80 percent filled.

According to the present invention, the cyanoacrylate adhesive compositions with the desired level of high viscosity are sterilized. The sterilization can be accomplished by common techniques, and is preferably accomplished by methods including, but not limited to, chemical, physical, and irradiation methods. Examples of chemical methods include, but are not limited to, exposure to ethylene oxide. Examples of irradiation methods include, but are not limited to, gamma irradiation, electron beam irradiation (E-beam), and microwave irradiation.

In preferred embodiments of the present invention, E-beam is used to sterilize the cyanoacrylate adhesive compositions with the desired level of viscosity. An initial fluence of the E-beam radiation is maintained at a minimum of 2 μCurie/$cm^2$. Preferably, the E-beam radiation has an initial fluence of from about 2 to 25 μCurie/$cm^2$. The dose of E-beam irradiation applied should be sufficient enough to sterilize both the package and the adhesive inside. The E-beam irradiation can be in a suitable dosage of from about 5 to 50 kGy, and more preferably from about 12 to 25 kGy. E-beam irradiation is preferably conducted at ambient atmosphere conditions and the exposure time to the irradiation is preferably within 60 seconds.

In order to reduce the bioburden, the cyanoacrylate adhesive compositions with the desired level of high viscosity can be filtered through a 0.2 μm filter prior to sterilization. The applicators with the overpack may also be sterilized with heat, ethylene oxide and heat prior to the final E-beam irradiation.

The entire package elements and adhesive inside are preferably sterile. The sterility of the cyanoacrylate adhesive compositions with the desired level of high viscosity may be analyzed by Bacteriostasis and Fungistasis tests. In embodiments of the present invention, a Sterility Assurance Level (SAL) should be obtained at a minimum of $10^{-3}$. In more preferred embodiments, the Sterility Assurance Level may be at least $10^{-6}$.

The present invention discloses stable, sterile cyanoacrylate compositions with the desired level of high viscosity, which are especially suitable for use in medical applications. In use, the cyanoacrylate adhesive composition is applied to the desired tissue area as a liquid which then polymerizes upon contact with tissue. The desired high viscosity of said cyanoacrylate adhesive compositions prevents the runniness of the adhesives encountered by the low viscous adhesive compositions.

The following non-limiting examples are intended to further illustrate the present invention.

EXAMPLE 1

To a three neck round bottom flask equipped with a thermometer and a magnetic stir bar, 118 g of 2-octyl cyanoacrylate monomer stabilized with BHA and $SO_2$ was mixed with 189 mg of pluronic F127 and stirred at 60° C. for 2 hours. After it cools down, the resulting cyanoacrylate adhesive composition was subjected to viscosity and set time test. The average set time for the sample is 17 s and the average viscosity for the sample is 58.9 cp.

EXAMPLE 2

To a three neck round bottom flask equipped with a thermometer and a magnetic stir bar, 128 g of 2-octyl cyanoacrylate monomer was mixed with small amounts of BHA and $SO_2$ and stirred at room temperature for 2 hours. Then 90 mg of pluronic F68 was added and stirred at 60° C. for 3 hours. After cooling down to room temperature, 474 mg of BHA, 12.2 ppm of $SO_2$ and 7.8 ppm of D&C Violet were added and the resulting cyanoacrylate adhesive composition was subjected to viscosity and set time test. The average set time for the sample is 25 s and the average viscosity for the sample is 24.5 cp.

EXAMPLE 3

To a three neck round bottom flask equipped with a thermometer and a magnetic stir bar, 119.6 g of 2-octyl cyanoacrylate monomer stabilized with BHA and $SO_2$ was mixed with 227 mg of pluronic F127 and stirred at 60° C. for 2 hours. After it cools down, the resulting cyanoacrylate adhesive composition was subjected to viscosity and set time test. The average set time for the sample is 21 s and the average viscosity for the sample is 123.4 cp.

EXAMPLE 4

To a three neck round bottom flask equipped with a thermometer and a magnetic stir bar, 109 g of the 2-octyl cyanoacrylate monomer was mixed with small amounts of BHA and $SO_2$ and stirred at room temperature for half an hour. Then 142 mg of pluronic F68 was added and stirred at 60° C. for 1 hour. After cooling down to 40° C., 294 mg of BHA, $SO_2$ and D&C Violet were added and the resulting cyanoacrylate adhesive composition was subjected to viscosity and set time test. The average set time for the sample is 31 s and the average viscosity for the sample is 39.2 cp.

EXAMPLE 5

To a three neck round bottom flask equipped with a thermometer and a magnetic stir bar, 109.7 g of the 2-octyl cyanoacrylate monomer was mixed with a small amount of $SO_2$ and stirred at room temperature for 1.5 hours. Then 132 mg of pluronic F38 was added and stirred at 60° C. for 2 hours. After cooling down to room temperature, BHA, $SO_2$ and D&C Violet were added and the resulting cyanoacrylate adhesive composition was subjected to viscosity and set time test. The average set time for the sample is 22 s and the average viscosity for the sample is 52.7 cp.

EXAMPLE 6

To a two neck round bottom flask equipped with a thermometer and a magnetic stir bar, 103.3 g of 2-octyl cyanoacrylate monomer in the presence of BHA and $SO_2$ was mixed with 124 mg of pluronic F127 and stirred at 60° C. for 2 hours. After it cools down, the resulting cyanoacrylate adhesive composition was subjected to viscosity and set time test. The average set time for the sample is 16 s and the average viscosity for the sample is 343.4 cp.

EXAMPLE 7

To a three neck round bottom flask equipped with a thermometer and a magnetic stir bar, 176.2 g of 2-octyl cyanoacrylate monomer stabilized with BHA and $SO_2$ was mixed with 705 mg of pluronic F68 and stirred at 60° C. for 1.5 hours. After it cools down, the resulting cyanoacrylate adhesive composition was subjected to viscosity and set time test. The average set time for the sample is 12 s and the average viscosity for the sample is 182.5 cp.

EXAMPLE 8

To a three neck round bottom flask equipped with a thermometer and a magnetic stir bar, 144.7 g of 2-octyl cyanoacrylate monomer stabilized with BHA and $SO_2$ was mixed with 289 mg of pluronic F38 and stirred at 60° C. for 1.5 hours. After it cools down, highly viscous 2-octyl cyanoacrylate gel was obtained.

EXAMPLE 9

To a three neck round bottom flask equipped with a thermometer and a magnetic stir bar, 111.5 g of 2-octyl cyanoacrylate monomer stabilized with BHA and $SO_2$ was mixed with 245 mg of pluronic F127 and stirred at 60° C. for 2 hours. After it cools down, highly viscous 2-octyl cyanoacrylate gel was obtained.

EXAMPLE 10

In a polyethylene bottle equipped with a magnetic stir bar, 33.9 g of 2-octyl cyanoacrylate gel was mixed with 90.4 of 2-octyl cyanoacrylate monomer stabilized with BHA and $SO_2$ and stirred at room temperature for 5 hours. The average viscosity of the cyanoacrylate compositions thus prepared is 66.8 cp.

EXAMPLE 11

To a three neck round bottom flask equipped with a thermometer and a magnetic stir bar, 114.8 g of 2-octyl cyanoacrylate monomer stabilized with BHA and $SO_2$ was mixed with 628 mg of pluronic F108 NF and stirred at 60° C. for 2 hours. After cooling down to room temperature, 2-octyl cyanoacrylate gel was obtained.

EXAMPLE 12

To a polyethylene bottle equipped with a magnetic stir bar, 50 g of 2-octyl cyanoacrylate gel was mixed with 53.6 g of 2-octyl cyanoacrylate monomer and stirred at room temperature for 6 hours. The average set time and viscosity for the sample are 15 s and 57.1 cp, respectively.

EXAMPLE 13

In a 2.5 gallon high density polyethylene (HDPE) container, 6.23 lbs of 2-octyl cyanoacrylate gel was mixed with 7.59 lbs of 2-octyl cyanoacrylate monomer stabilized with BHA and $SO_2$ and blended with a mechanic stirrer at room temperature for 7 hours. The average set time and viscosity for the sample are 42 s and 62.5 cp, respectively.

EXAMPLE 14

To a polyethylene bottle equipped with a magnetic stir bar, 78 g of 2-octyl cyanoacrylate with a viscosity of about 110 cps was mixed with 33 g of n-butyl cyanoacrylate monomer and 0.56 g of diisodecyl adipate, which were stirred at room temperature for 6 hours. The average viscosity for the sample is 40.6 cp.

EXAMPLE 15

To a three neck round bottom flask equipped with a thermometer and a magnetic stir bar, 278 g of 2-octyl cyanoacrylate monomer stabilized with small amounts of BHA and $SO_2$ was mixed with 306 mg of pluronic F68 and stirred at 50° C. for 2 hours. The resulting solution was stabilized with BHA and $SO_2$ and filtered by filtration flask to provide a cyanoacrylate adhesive composition with the viscosity about 45 cp. More stabilizers were added to the composition, which include 200 ppm of hydroquinone, 10 ppm of Sulfuric acid, 200 ppm of Acetic acid, and 80 more ppm of $SO_2$. 5% of tributyl citrate was added as the plasticizer.

EXAMPLE 16

2-Octyl cyanoacrylate gel was diluted with 2-octyl cyanoacrylate monomer to provide an adhesive composition with a viscosity about 80 cp which was primarily stabilized with BHA and $SO_2$. The composition was further stabilized with additional stabilizers including 300 ppm more of BHA, 5 ppm of Sulfuric acid, 200 ppm of 4-Methoxyphenol, and 300 ppm of Acetic acid. The composition was packaged, sterilized and tested for stability.

EXAMPLE 17

A diluted 2-octyl cyanoacrylate composition with the viscosity of about 47 cp was stabilized with BHA as the free radical inhibitor and $SO_2$ as the anion inhibitor. In order to extend the stability of the composition, 500 ppm of 4-Methoxyphenol, 5 ppm of Sulfuric acid, 10 more ppm of $SO_2$ and 200 ppm of Acetic acid were further added to the adhesive composition. In addition, 1% of diisodecyl adipate was added as a plasticizer.

EXAMPLE 18

To a three neck round bottom flask equipped with a thermometer and a magnetic stir bar, 301 g of 2-octyl cyanoacrylate monomer stabilized with BHA and $SO_2$ was mixed with 436 mg of pluronic F68 and stirred at 55° C. for 2 hours. The resulting solution was stabilized with BHA and $SO_2$ and filtered by filtration flask to provide a cyanoacrylate adhesive composition with the viscosity about 44 cps. 5% of acetyl tributyl citrate was added as the biocompatible plasticizer. More stabilizers were added to the composition, which include 10 ppm of Sulfuric acid, 200 ppm of Acetic acid, 500 ppm of 4-Methoxyphenol, and 80 more ppm of $SO_2$.

EXAMPLE 19

To a polyethylene bottle equipped with a magnetic stir bar, 2500 ppm of BHT and 1000 ppm of Acetic acid as the additional stabilizers were added to 28 g of 2-octyl cyanoacrylate composition with a viscosity at about 35 cp which was primarily stabilized with BHA and $SO_2$.

EXAMPLE 20

2-Octyl cyanoacrylate gel was diluted with 2-octyl cyanoacrylate monomer in the presence of BHA and $SO_2$ to provide an adhesive composition with a viscosity of 130 cp. The adhesive composition was mixed with additional stabilizers including 5 ppm of Sulfiric acid, 200 ppm of Acetic acid, 2500 ppm of BHT, and 40 more ppm of $SO_2$. The composition was mixed with 15% of diisodecyl adipate as the plasticizer and 270 ppm of 18-crown-6 as the accelerator.

EXAMPLE 21

To a three neck round bottom flask equipped with a thermometer and a magnetic stir bar, 273 g of 2-octyl cyanoacrylate monomer stabilized with a small amount of $SO_2$ was mixed with 317 mg of pluronic F68 and stirred at 48° C. for 2 hours. The resulting solution was stabilized with BHA and $SO_2$ and filtered by filtration flask to provide a cyanoacrylate adhesive composition with the viscosity about 79 cps. Stabilizers were added to the adhesive composition, which include 5 ppm of Sulfuric acid, 200 ppm of Acetic acid, 2500 ppm of BHT, and 80 more ppm of $SO_2$. 18-crown-6 as was used as the accelerator and 10% of acetyl tributyl citrate was included as the plasticizer.

EXAMPLE 22

Highly viscous 2-octyl cyanoacrylate gel was diluted with 2-octyl cyanoacrylate monomer in the presence of BHA and $SO_2$ to provide an adhesive composition with a viscosity of about 90 cp. The resulting adhesive composition was stirred at 60° C. for 2 hours, then mixed with additional stabilizers including 200 ppm of Sultone, 500 ppm of Acetic acid, 3000 ppm of BHT, 2000 ppm of MP, 1500 ppm of Hydroquinone, and 80 more ppm of $SO_2$.

EXAMPLE 23

In a polyethylene bottle equipped with a magnetic stir bar, a diluted 2-octyl cyanoacrylate composition with the viscosity of about 72 cp was stabilized with BHA as the free radical inhibitor and $SO_2$ as the anion inhibitor. Other stabilizers were further added to the adhesive composition including 200 ppm of Sultone, 5 ppm of Sulfuric acid, 500 ppm of Acetic acid, 3000 ppm of BHT, 2000 ppm of MP, 1500 ppm of Hydroquinone, and 80 more ppm of S02. Acetyl tributyl citrate was added as the plasticizer in the amount of 5%.

What is claimed is:

1. A liquid adhesive composition comprising:

from 94.27 weight % to 99.92 weight % of at least one liquid cyanoacrylate monomer;

at least one free radical stabilizer;

at least one anionic stabilizer; and from 0.01 weight % to 0.50 weight % of at least one poloxamer selected from the group consisting of:

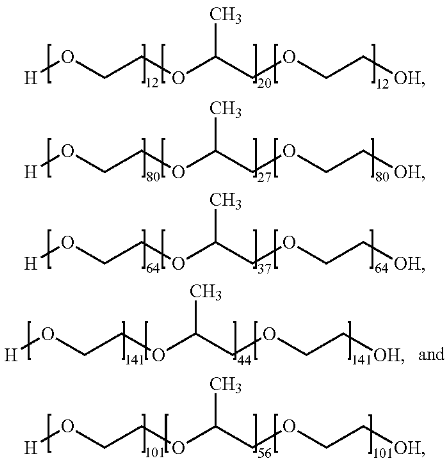

wherein the at least one poloxamer is dissolved in the liquid cyanoacrylate monomer.

2. The composition of claim 1 wherein the cyanoacrylate monomer is a cyanoacrylate ester monomer.

3. The composition of claim 2 wherein the cyanoacrylate ester monomer is selected from the group consisting of alkyl, cycloalkyl or alkylalkoxyl cyanoacrylate monomer.

4. The composition of claim 3 wherein the cyanoacrylate ester monomer is 2-cyanoacrylate ester.

5. The composition of claim 1 wherein the at least one poloxamer is present in an amount of from about 0.07% to about 0.16% by weight of cyanoacrylate.

6. The composition of claim 1 wherein the anionic stabilizer is selected from the group consisting of sulfur dioxide, boron oxide, phosphoric acid, acetic acid, benzoic acid, cyanoacetic acid, 1,4-butane sultone, boron trifluoride, perchloric acid, hydrochloric acid, surfuric acid, sulfonic acid and mixtures thereof.

7. The composition of claim 6 wherein the anionic stabilizer is 1,4-butane sultone in an amount of from about 100 to 3000 ppm.

8. The composition of claim 6 wherein the anionic stabilizer is sulfur dioxide in an amount of from about 10 to 500 ppm.

9. The composition of claim 6 wherein the anionic stabilizer is sulfuric acid in an amount of from about 2 to 30 ppm.

10. The composition of claim 6 wherein the anionic stabilizer is acetic acid in an amount of about from 200 to 4000 ppm.

11. The composition of claim 1 wherein the free radical stabilizers are selected from the group consisting of butylated hydroxyanisole, hydroquinone (HQ), catechol, hydroquinone monomethyl ester, butylated hydroxytoluene (BHT), 4-ethoxyphenol, 4-methoxyphenol and mixtures thereof.

12. The composition of claim 11 wherein the free radical stabilizer is butylated hydoxyanisole in an amount of from about 3000 to 15000 ppm.

13. The composition of claim 11 wherein the free radical stabilizer is hydroquinone in an amount of from about 50 to 3000 ppm.

14. The composition of claim 11 wherein the free radical stabilizer is 4-methoxyphenol in an amount of from about 200 to 5000 ppm.

15. The composition of claim 11 wherein the free radical stabilizer is butylated hydroxytoluene in an amount of from about 2000 to 10000 ppm.

16. The composition of claim 1 further comprising a plasticizer in an amount of from about 0.50% to about 20%.

17. The composition of claim 1 wherein the viscosity of the composition measured after 12 days in an accelerated aging test at 80° C. is from about 100% to about 150% of the viscosity of the composition measured at time zero.

18. The composition of claim 17 wherein the composition is sterilized by a method selected from the group consisting of gamma irradiation, electron beam irradiation, and microwave irradiation.

19. The composition of claim 1 wherein the viscosity is from about 10 to about 300,000 cp.

20. The composition of claim 19 wherein the viscosity is from about 10 to about 1000 cp.

21. The composition of claim 20 wherein the viscosity is from about 20 to about 500 cp.

22. The composition of claim 21 wherein the viscosity is from about 30 to about 300 cp.

23. The composition of claim 1 wherein the at least one liquid cyanoacrylate monomer is present in the composition at from 98.93 weight % to 99.92 weight %.

24. The composition of claim 1 wherein the at least one liquid cyanoacrylate monomer is present in the composition at from 99.20 weight % to 99.92 weight %.

25. A liquid adhesive composition comprising from 94.27 weight % to 99.92 weight % of at least one liquid cyanoacrylate monomer and from 0.01 weight % to 0.50 weight % of at least one poloxamer selected from the group consisting of:

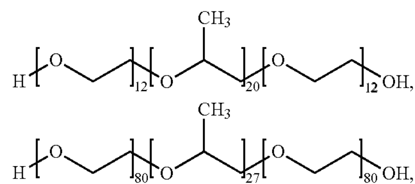

-continued

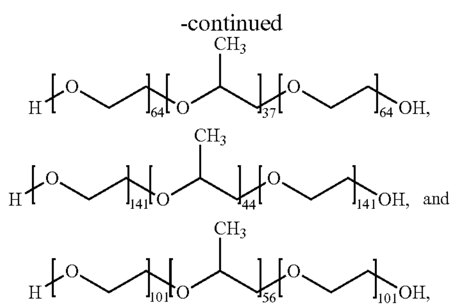

wherein the at least one poloxamer is dissolved in the liquid cyanoacrylate monomer, wherein the liquid adhesive composition is made by a process comprising: adding at least one poloxamer to a composition comprising at least one liquid cyanoacrylate monomer, at least one free radical stabilizer, and at least one anionic stabilizer; and mixing the composition at a temperature of from 30° C. to 70° C.

26. The composition of claim 25 wherein the temperature of the mixing step is from 40° C. to 65° C.

27. The composition of claim 25 wherein the temperature of the mixing step is from 50° C. to 60° C.

28. The composition of claim 25 wherein the cyanoacrylate monomer is a cyanoacrylate ester monomer.

29. The composition of claim 28 wherein the cyanoacrylate ester monomer is selected from the group consisting of alkyl, cycloalkyl or alkylalkoxyl cyanoacrylate monomer.

30. The composition of claim 28 wherein the cyanoacrylate ester monomer is 2-cyanoacrylate ester.

31. The composition of claim 25 wherein the at least one poloxamer is present in an amount of from about 0.07% to about 0.16% by weight of cyanoacrylate.

32. The composition of claim 25 wherein the anionic stabilizer is selected from the group consisting of sulfur dioxide, boron oxide, phosphoric acid, acetic acid, benzoic acid, cyanoacetic acid, 1,4-butane sultone, boron trifluoride, perchloric acid, hydrochloric acid, surfuric acid, sulfonic acid and mixtures thereof.

33. The composition of claim 32 wherein the anionic stabilizer is 1,4-butane sultone in an amount of from about 100 to 3000 ppm.

34. The composition of claim 32 wherein the anionic stabilizer is sulfur dioxide in an amount of from about 10 to 500 ppm.

35. The composition of claim 32 wherein the anionic stabilizer is sulfuric acid in an amount of from about 2 to 30 ppm.

36. The composition of claim 32 wherein the anionic stabilizer is acetic acid in an amount of about from 200 to 4000 ppm.

37. The composition of claim 31 wherein the free radical stabilizers are selected from the group consisting of butylated hydroxyanisole, hydroquinone (HQ), catechol, hydroquinone monomethyl ester, butylated hydroxytoluene (BHT), 4-ethoxyphenol, 4-methoxyphenol and mixtures thereof.

38. The composition of claim 37 wherein the free radical stabilizer is butylated hydoxyanisole in an amount of from about 3000 to 15000 ppm.

39. The composition of claim 37 wherein the free radical stabilizer is hydroquinone in an amount of from about 50 to 3000 ppm.

40. The composition of claim 37 wherein the free radical stabilizer is 4-methoxyphenol in an amount of from about 200 to 5000 ppm.

41. The composition of claim 37 wherein the free radical stabilizer is butylated hydroxytoluene in an amount of from about 2000 to 10000 ppm.

42. The composition of claim 25 further comprising a plasticizer in an amount of from about 0.50% to about 20%.

43. The composition of claim 25 wherein the viscosity of the composition measured after 12 days in an accelerated aging test at 80° C. is from about 100% to about 150% of the viscosity of the composition measured at time zero.

44. The composition of claim 31 wherein the processes further comprises the step of sterilizing the composition by a method selected from the group consisting of gamma irradiation, electron beam irradiation, and microwave irradiation.

45. The composition of claim 25 wherein the viscosity is from about 10 to about 300,000 cp.

46. The composition of claim 45 wherein the viscosity is from about 10 to about 1000 cp.

47. The composition of claim 46 wherein the viscosity is from about 20 to about 500 cp.

48. The composition of claim 47 wherein the viscosity is from about 30 to about 300 cp.

49. The composition of claim 25 wherein the at least one liquid cyanoacrylate monomer is present in the composition at from 98.93 weight % to 99.92 weight %.

50. The composition of claim 25 wherein the at least one liquid cyanoacrylate monomer is present in the composition at from 99.20 weight % to 99.92 weight %.

* * * * *